United States Patent [19]

Herron

[11] Patent Number: 4,764,521

[45] Date of Patent: Aug. 16, 1988

[54] LEUKOTRIENE ANTAGONISTS AND A METHOD OF USE THERE AS

[75] Inventor: David K. Herron, Indianapolis, Ind.

[73] Assignee: Eli Lilly and Company, Indianapolis, Ind.

[21] Appl. No.: 860,723

[22] Filed: May 7, 1986

Related U.S. Application Data

[62] Division of Ser. No. 514,394, Jul. 18, 1983, abandoned.

[51] Int. Cl.$^4$ .................. A61K 31/41; A61K 31/19; C07D 257/04; C07D 257/06; C07C 65/21
[52] U.S. Cl. .................................. 514/381; 514/571; 548/251; 548/253; 562/464; 562/471
[58] Field of Search ............... 548/253, 251; 562/471, 562/464; 514/381, 571

[56] References Cited

U.S. PATENT DOCUMENTS 4,499,299  2/1985  Bernstein et al. ................... 514/570

FOREIGN PATENT DOCUMENTS

| 1124296 | 2/1962 | Fed. Rep. of Germany . |
| 4722 | 2/1967 | France . |
| 2509725 | 1/1983 | France . |
| 758980 | 10/1956 | United Kingdom . |
| 785049 | 10/1957 | United Kingdom . |
| 793513 | 4/1958 | United Kingdom . |
| 793230 | 4/1958 | United Kingdom . |
| 804565 | 11/1958 | United Kingdom . |
| 810154 | 3/1959 | United Kingdom . |
| 883255 | 11/1961 | United Kingdom . |
| 1111361 | 4/1968 | United Kingdom . |
| 1591063 | 6/1981 | United Kingdom . |

*Primary Examiner*—Glennon H. Hollrah
*Assistant Examiner*—D. B. Springer
*Attorney, Agent, or Firm*—Robert A. Conrad; Leroy Whitaker

[57] ABSTRACT

This invention provides novel compounds which are leukotriene antagonists, certain novel intermediates to the compounds, formulations of the compounds, and a method of using the compounds for the treatment of conditions characterized by an excessive release of leukotrienes.

18 Claims, No Drawings

LEUKOTRIENE ANTAGONISTS AND A METHOD OF USE THERE AS

This application is a division of application Ser. No. 514,394, filed July 18, 1983, abandoned.

BACKGROUND OF THE INVENTION

Research in the area of allergic reactions of the lung has provided evidence that arachidonic acid derivatives formed by the action of lipoxygenases are related to various disease states. Some of these arachidonic acid metabolites have been classified as members of a family of eicosatetraenoic acids termed leukotrienes. Three of these substances are currently thought to be major components of what has been previously called slow reacting substance of anaphylaxis (SRS-A).

It is the object of this invention to provide novel chemical agents which are selective leukotriene antagonists that can be used therapeutically in the treatment of allergic disorders such as asthma, where leukotrienes are thought to be causal mediators.

SUMMARY OF THE INVENTION

This invention provides for compounds of the Formula I

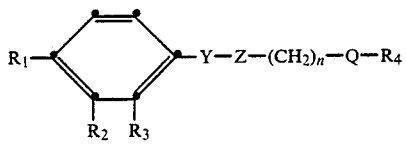

and pharmaceutically acceptable salts thereof, wherein:

$R_1$ is

or halo;
$R_2$ is halo or hydroxy;
$R_3$ is $C_1-C_{12}$ alkyl, hydroxy-substituted $C_1-C_{12}$ alkyl, or $C_2-C_6$ alkenyl;
Y is —O—,

or —$CR_6R_7$—;
Z is —O—,

or —$CR_8R_9$—,
or when taken together, —Y—Z— is —CH=CH—;
n is 1—10;
Q is —O—, —NR—,

or a bond $R_4$ is —$COR_{10}$, hydroxy, —$NR_{11}R_{12}$, —SC(=NH)$NH_2$, or

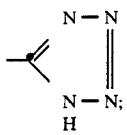

where
R is hydrogen or $C_1-C_3$ alkyl;
$R_5$ is hydrogen, $C_1-C_6$ alkyl, $C_3-C_8$ cycloalkyl, or phenyl optionally substituted with halo, $C_1-C_4$ alkyl, or $C_1-C_4$ alkoxy;
each of $R_6$, $R_7$, $R_8$, and $R_9$ is independently hydrogen, $C_1-C_{10}$ alkyl, phenyl, or benzyl;
$R_{10}$ is hydroxy, $C_1-C_4$ alkoxy, —NHOH, or —$NR_{11}R_{12}$;
each of $R_{11}$ and $R_{12}$ is independently hydrogen, $C_1-C_3$ alkyl, or when taken together with the nitrogen atom form a morpholine or N-methyl piperazine ring; and
p is 0, 1, or 2;
with the provisions that:
(a) when $R_1$ is

$R_2$ may not be hydroxy;
(b) when one of Y and Z is —O— or

the other of Y and Z may not be —O— or

and
(c) when $R_4$ is $COR_{10}$, hydroxy, —$NR_{11}R_{12}$, or —SC(=NH)$NH_2$1Q may only be a bond.

Further provided by this invention is a method for treating immediate hypersensitivity conditions such as asthma, using compounds of Formula I above and pharmaceutical formulations for these compounds.

Also provided by this invention are novel intermediates useful in preparing certain compounds of Formula I. These intermediates are represented by the

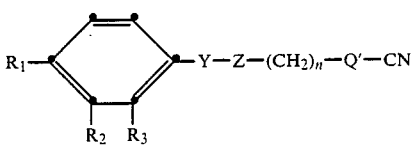

wherein:
$R_1$ is

or halo;

R$_2$ is halo or hydroxy;
R$_3$ is C$_1$–C$_{12}$ alkyl, hydroxy-substituted C$_1$–C$_{12}$ alkyl, or C$_2$–C$_6$ alkenyl;
Y is —O—,

or —CR$_6$R$_7$—
Z is —O—

—CR$_8$R$_9$—,
or when taken together, —Y—Z— is —CH=CH—;
n is 1–10; and
Q' is —S— or a bond; where
R$_5$ is hydrogen. C$_1$–C$_8$ cyclo alkyl, or phenyl optionally substituted with halo, C$_1$–C$_{10}$ alkyl, phenyl, or benzyl; and
p is 0, 1, or 2;
with the provisions that:
(a) when R$_1$ is

R$_2$ may not be hydroxy; and
(b) when one of Y and Z is —O— or

other of Y and Z mayu not be —O—

DETAILED DESCRIPTION AND THE PREFERRED EMBODIMENT

The present invention relate to new organic compounds that are useful in the treatment of immediate hypersensitivity reactions. A prepared group of compounds are the compound of Forumula I wherein:
(a) R$_1$ is halo, especialy chloro;
(b) R$_2$ is halo, especially chloro;
(c) R$_3$ is C$_1$–C$_6$ alkyl especially propyl,
(d) Y is O—.
(e) Z is —CR$_8$R$_9$—especially CH$_2$—
(f) Q is —O—a bond, or —S—(p is O),
(g) R$_4$ is 5-tetrazolyl or —COOH, and
(h) n is 1–4.
An especially preferred group of compounds are those of the formula Ia

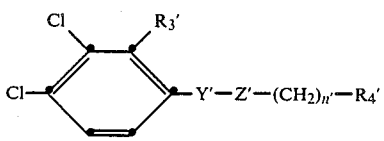

and pharmaceutically acceptable salts thereof wherein:

R$_3$' is C$_1$–C$_6$ alkyl, especially propyl;
each of Y' and Z' is independently —O—,

or —CH$_2$—, except that when one of Y' and Z' is —O— or

the other of Y' and Z' may not be —O— or

n' is 2 or 3; and
R$_4$' is —COOH, 5-tetrazolyl, or 5-thiotetrazolyl.

The following definitions refer to the various terms used throughout this disclosure.

The term "C$_1$–C$_{12}$ alkyl" refers to the straight and branched aliphatic radicals of 1 to 12 carbon atoms such as methyl, ethyl, propyl, isopropyl, butyl, isobutyl, sec-butyl, tert-butyl, amyl, isoamyl, sec-amyl, sec-isoamyl (1,2-dimethylpropyl), tert-amyl (1,1-dimethylpropyl), hexyl, isohexyl (4-methylpentyl), sec-hexyl (1-methylpentyl), 2-methylpentyl, 3-methylpentyl, 1,1-dimethylbutyl, 2,2-dimethylbutyl, 3,3dimethylbutyl, 1,2-dimethylbutyl, 1,3-dimethylbutyl, 1,2,2-trimethylpropyl, 1,1,2-trimethylpropyl, heptyl, isoheptyl (5-methylhexyl), sec-heptyl (1-methylhexyl), 2,2-dimethylpentyl, 3,3-dimethylpentyl, 4,4-dimethylpentyl, 1,2-dimethylpentyl, 1,3-dimethylpentyl, 1,4dimethylpentyl, 1,2,3-trimethylbutyl, 1,1,2-trimethylbutyl, 1,1,3-trimethylbutyl, octyl, isooctyl (6-methylheptyl), sec-octyl (1-methylheptyl), tert-octyl (1,1,3,3-tetramethylbutyl), nonyl, 1-, 2-, 3-, 4-, ethylheptyl, 1-, 2-, or 3-propylhexyl, decyl, 1-, 2-, 3-, 4-, 5-, 6-, 7-, or 8-methylnonyl, 1-, 2-, 3-, 4-, 5-, or 6-ethyloctyl, 1-, 2-, 3-, or 4-propylheptyl, undecyl, dodecyl, and the like. The term "C$_1$–C$_{12}$ alkyl" includes within its definition the terms "C$_1$–C$_3$ alkyl", "C$_1$–C$_4$ alkyl", and "C$_1$–C$_6$ alkyl".

The term "C$_3$–C$_8$ cycloalkyl" refers to the saturated alicyclic rings of three to eight carbon atoms such as cyclopropyl, methylcyclopropyl, cyclobutyl, cyclopentyl, cyclohexyl, cyclooctyl, and the like.

The term "C$_2$–C$_6$ alkenyl" refers to straight and branched radicals of two to six carbon atoms such as ethenyl, allyl, isopropenyl, butenyl, isobutenyl, 3-methyl-2-butenyl, n-hexenyl, and the like, and includes the term "C$_3$–C$_6$ alkenyl".

The term "halo" refers to fluoro, chloro, bromo, and iodo. The term "C$_1$–C$_4$ alkoxy" refers to straight and branched alkoxy radicals of up to four carbon atoms such as methoxy, ethoxy, n-propoxy, isopropoxy, n-butoxy, tert-butoxy, and the like.

The pharmaceutically acceptable base addition salts of this invention include salts derived from inorganic bases, such as ammonium and alkali and alkaline earth metal hydroxides, carbonates, bicarbonates, and the like, as well as salts derived from non-toxic basic organic amines, such as aliphatic and aromatic amines, aliphatic diamines, hydroxy alkylamines, and the like. Such bases useful in preparing the salts of this invention thus include ammonium hydroxide, potassium carbonate, sodium bicarbonate, calcium hydroxide, methyl amine, diethyl amine, ethylene diamine, cyclohexylamine, ethanolamine, and the like. The potassium and sodium salt forms are particularly preferred.

In addition, when the compounds of formula I are amine derivatives (e.g., $R_4$ is $-NR_{11}R_{12}$ or $-SC(=NH)NH_2$), the compounds may also exist as the corresponding acid addition salts. The pharmaceutically acceptable acid addition salts of this invention therefore also include salts derived from inorganic acids such as hydrochloric acid, nitric acid, phosphoric acid, sulfuric acid, hydrobromic acid, hydriodic acid, phosphorous acid and the like, as well as salts derived from nontoxic organic acids such as aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, $\beta$-hydroxybutyrate, glycollate, malate, tartrate, methanesulfonate, propanesulfonate, naphthalene-1-sulfonate, naphthalene-2-sulfonate, and the like salts. Salts from inorganic acids are preferred, especially the hydrochloride or hydrobromide salts.

It is recognized that if $R_6$ is different from $R_7$, or $R_8$ is different from $R_9$, various stereoisomers will exist. This invention is not limited to any particular stereoisomer but includes all possible individual isomers and racemates of the compounds of Formula I. Similarly, when $-Y-Z-$ is $-CH=CH-$, both the individual cis and trans isomers and their mixture are included as part of this invention.

Some of the compounds of this invention may be prepared by the reaction of a compound of the formula

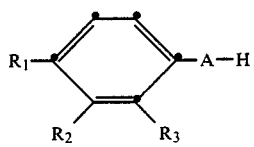

II wherein A is $-O-$ or $-S-$, with a compound of the formula

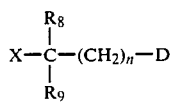

III wherein X is a suitable leaving group, such as halo, preferably chloro, and D is $-Q-R_4$, a precursor of $-Q-R_4$, halo, cyano, thiocyano, or a protected acid ester such as a benzhydryl ester. This procedure is useful in preparing the compounds of this invention designated by Formula I'

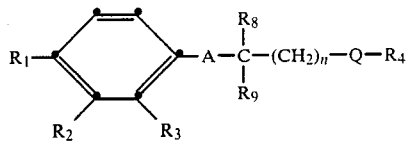

I' either directly (when D is $Q-R_4$) or indirectly from intermediates IV

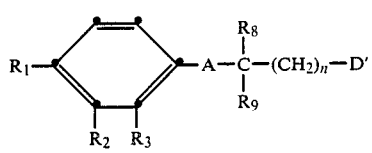

IV wherein D' is a precursor to $-Q-R_4$, halo, cyano, thiocyano, or a protected acid ester.

The reaction between compounds II and III is usually performed in equimolar amounts although ratios other than equimolar amounts are completely operative. The reaction is best carried out in a nonreactive solvent such as ketones, especially acetone or methyl ethyl ketone, and in the presence of a base, preferably an alkali metal hydroxide or carbonate, preferably potassium carbonate. Especially when X is chloro, a catalyst such as potassium or sodium iodide may be added to increase the reaction rate. The reaction may be carried out at temperatures of about ambient temperature up to the boiling point of the reaction mixture, the latter being preferred.

In the case where D (D') is cyano, the resulting intermediate IV may be converted to the compounds of this invention by the following methods. Compounds of Formula I' wherein $R_4$ is $-COOH$ may be obtained by hydrolysis of the intermediate cyano derivative. This is generally accomplished by heating the cyano derivative in aqueous alcohols in the presence of a base such as sodium hydroxide. Alternatively, the carboxylic acid derivatives (I', $R_4$ is $-COOH$) may be prepared by the hydrolysis of the corresponding ester derivatives. This may be accomplished by an aqueous hydrolysis as described above or, especially in the case of a diphenylmethyl (benzhydryl) ester, using methods known in the art such as treating with formic acid and triethylsilane followed by an aqueous workup, acidic hydrolysis, treatment with trifluoroacetic acid in anisole, or catalytic hydrogenation. The required benzhydryl ester starting materials (III, D is a benzhydryl ester) may be prepared from the corresponding carboxylic acids (III, D is $-COOH$) in the usual ways, such as treatment with diphenyldiazomethane in methylene chloride or heating with benzhydrol and a mineral acid in a solvent such as toluene with the azeotropic removal of water. The compounds of Formula I' wherein $R_4$ is $-COO(C_1-C_4$ alkyl) may be prepared by conventional methods of esterification from the respective acid derivatives or are prepared directly by the methods described below. Salts may be prepared by treating the corresponding acids ($R_4$ is $-COOH$) with an appropriate base in the normal manner. Amide derivatives ($R_4$ is $-CONR_{11}R_{12}$ or $-CONHOH$) may be prepared by direct aminolysis of the corresponding ester, or from the corresponding carboxylic acid using conventional means such as conversion to the acid chloride followed by reaction of the acid chloride with an appropriate amine or treatment with an agent such as 1,1'-carbonyldiimidazole in the presence of an appropriate amine. In either case, the ester or acid is reacted with the appropriate amine V $$HNR_{11}R_{12} \quad\quad V$$

wherein $R_{11}$ and $R_{12}$ are as described hereinabove, or hydroxylamine, the latter giving the hydroxamic acid derivative.

The compounds of Formula I' wherein $R_4$ is 5-tetrazolyl (Q is a bond) are prepared by treating the cyano intermediate with an alkali metal azide such as sodium azide, ammonium chloride, and (optionally) lithium chloride in a non-reactive high-boiling solvent such as N,N-dimethylformamide, preferably at temperatures from 60° C. to the reflux temperature of the reaction mixture. Alternatively, tetramethylguanidinium azide may be used in place of the alkali metal azide, ammonium chloride, and lithium chloride. The thiotetrazole compounds of Formula I'(Q is —S—) are prepared from the thiocyano intermediates in a similar manner or may be prepared from a halo intermediate (IV, D' is halo) on treatment with 5-mercaptotetrazole.

When employing intermediate III wherein D is halo, those skilled in the art will recognize that when the substituents $R_8$ and $R_9$ are both hydrogen, affording a symmetrically-substituted dihaloalkane III, X and D may be the same or different leaving groups since the reaction with compound II will give the same product IV regardless which "end" of the molecule reacts. However, when alkane III is non-symmetrically substituted, those skilled in the art will recognize that X should be a better leaving group than D (halo) in order for the desired product IV to be formed. If D is the better leaving group in compound III, III can first be converted to a different intermediate compound III (e.g., reaction of III (D is halo) with an alkali metal cyanide to give III (where D is —CN)) which can then be reacted with compound II as previously described.

The compounds of Formula IV wherein D' is halo may be transformed into the compounds of this invention in the following manner. When compounds of Formula IV (D' is halo) are heated with an alkali metal cyanide, such as sodium cyanide, in the presence of a high boiling, nonreactive solvent, such as N,N-dimethylformamide, at elevated temperatures (50° C. to the reflux temperature of the solvent), the intermediate cyano compound of Formula IV (D' is cyano) is produced which may then be transformed into the acid, ester, or tetrazole derivatives as described previously. Similarly, the thiotetrazole compounds of this invention can be prepared by reacting a compound of Formula IV (D' is halo) with an alkali metal thiocyanate in a similar manner to give the intermediate thiocyano compound of Formula IV (D' is —SCN) followed by transformation to the thiotetrazole in the usual manner. Alternatively, the thiotetrazole compounds may be prepared from IV (D' is halo) and 5-mercaptotetrazole in a similar manner as previously mentioned.

The compounds of Formula I' wherein $R_4$ is —OH may be prepared directly from the reaction of compound II and a haloalkanol (III, X is halo, D is —OH) or may be prepared from the intermediate IV where D' is halo by aqueous hydrolysis. These compounds may be transformed into other compounds or intermediates of this invention (e.g., where $R_4$ is —CN, etc.) by preparation of the mesylate derivative and displacing with a suitable nucleophile (such as cyanide ion).

The compounds of Formula I' wherein $R_4$ is —$NR_{11}R_{12}$ may be prepared by the reaction of the compounds of Formula IV where D' is halo with compounds of the Formula V. The reaction of compounds IV and V is generally carried out in the presence of a nonreactive, high-boiling solvent such as N,N-dimethylformamide, usually in the presence of a base, preferably an alkali metal carbonate or hydroxide, generally at elevated temperatures up to the boiling point of the solvent.

The isothiourea and thio-, amino-, and oxytetrazole compounds may be prepared from intermediate IV where D' is halo by reacting with thiourea and 5-mercapto-, 5-amino-, and 5-hydroxytetrazole, respectively. The reactions are performed by stirring the two reactants in a non-reactive solvent preferably at room to reflux temperature for about two to three days. In the thiourea reaction, ethanol is the preferred solvent and the product is usually isolated as the isothiuronium hydrohalide salt which is formed directly. In the tetrazole reactions, the preferred solvent is dimethylformamide and an acid scavenger, such as an alkali metal carbonate, is preferably included in the reaction.

Certain other compounds of this invention as defined by Formula I''

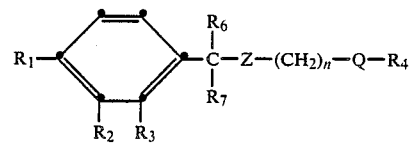

are prepared in a similar manner as taught for the compounds of Formula I'. The compounds of Formula I'' are prepared directly or indirectly by treating a bromo-compound of the Formula VI

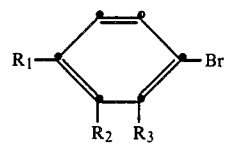

with a strong base, such as lithium diisopropylamide, in an inert solvent, such as diethyl ether, at low temperatures, preferably −20° to 0° C., to prepare the lithium salt of VI which is then reacted with III'

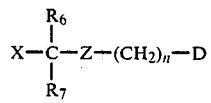

to provide compound I'' directly (when D is -Q-$R_4$) or compounds VII.

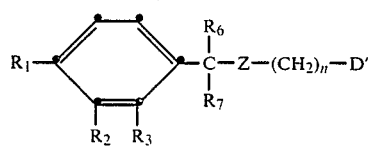

Compounds VII can then be transformed into I″ by the same methods of transformation as previously described for converting compounds IV into I′.

Alternately, when Z is —O— or —S—, certain compounds of Formula I″ may be prepared by reacting the appropriate benzyl derivative VIII

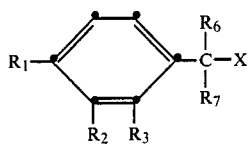

with a compound of the Formula IX

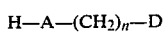

to give compounds I″(Z is —O— or —S—) directly or indirectly through intermediate VII.

An additional preparation of certain compounds of Formula I″(Z is —O— or —S—) involves the reaction of a benzyl compound XI

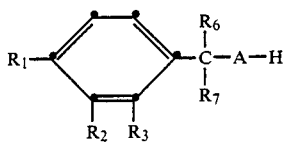

with a compound of Formula XII

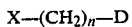

to similarly give compounds I″(Z is —O— or —S—) directly or indirectly through intermediates VII.

The alkene derivatives of this invention I‴

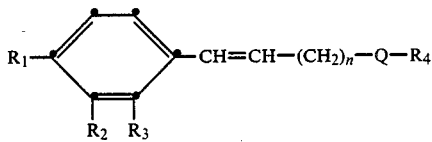

are prepared by reacting a Wittig reagent such as that represented by Formula XIII

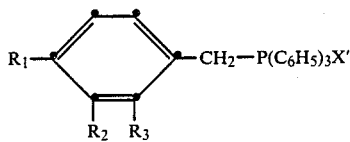

with an aldehyde of Formula XIV

wherein X′ is chloro, bromo, or iodo, to give either compounds I‴ directly (D is —Q—R$_4$) or indirectly (D is D′) through intermediates XV. The transformations of intermediate XV

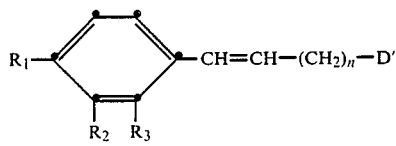

to compounds of Formula I‴ and the intraconversion of various compounds of Formula I‴ are the same as previously described for compounds I′ and I″. This sequence is limited as those skilled in the art will appreciate, to those aldehydes XIV which may be prepared and are stable to the reaction conditions. For those substituents D which are unstable in the presence of aldehydes and/or Wittig conditions, the desired substituent may be introduced from an intermediate aldehyde after transformation into compound XV. Additionally, the compounds of Formula I‴ may be converted to the compounds of Formula I wherein Y and Z taken together are —CH$_2$—CH$_2$—(R$_6$, R$_7$, R$_8$, and R$_9$ are all hydrogen) by the hydrogenation of I‴ by any of many methods known in the art.

Compounds I‴ and intermediates XV may also be produced from benzaldehyde XVI

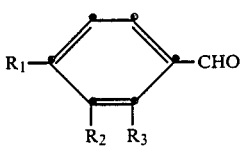

and Wittig reagent XVII

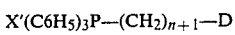

in the same manner as described above for compounds XIII and XIV. This allows for the preparation of those compounds which could not be made due to the incompatability of the D functionality and the aldehyde group in intermediate XIV.

The thio derivatives and intermediates of this invention (p is 0) may be transformed into the corresponding sulfoxide (p is 1) compounds upon treatment with a mild oxidizing agent, such as hydrogen peroxide in methanol or an alkali metal periodate in aqueous alcohol. The corresponding sulfones (p is 2) are prepared from the thio or sulfoxide compounds on treatment with a strong oxidizing agent such as hydrogen peroxide in acetic acid or m-chloroperbenzoic acid in methanol.

In addition, various compounds of Formula I can be prepared from other compounds, precursors, or intermediates of Formula I by standard methods such as hydrolysis, esterification, alkylation, oxidation, reduction, aminolysis, and the like, as are well known to those skilled in the art. In the prior discussion, the terms "precursor" and "precursor to —Q—R$_4$" mean those compounds, either related to the final compounds I or any intermediates or starting materials, which can be transformed into the desired functionality —Q—R$_4$. Those include the cyano intermediates and intermediates which may be transformed into the title products by any of the above mentioned methods known to those skilled in the art.

Other precursors to the products of this invention include phenyl compounds of Formula I wherein R$_1$, R$_2$ or R$_3$ are hydrogen. The desired substituents R$_1$, R$_2$ or R$_3$ can be introduced after the respective "halves" of the final compound have been coupled by methods previously described. These substituents can be introduced from the corresponding hydrogen substituted phenyl group by methods known in the art. For instance, the R$_1$ acyl substituents can be introduced following standard methods (e.g., Friedel-Crafts reaction), halo groups of R$_1$ and/or R$_2$ can be introduced by halogenation of the phenyl ring, $R_3$ groups can be introduced by direct alkylation of the phenyl ring, etc. Although this functionalization of the phenyl ring can be performed in certain cases as the last step in the chemical sequence, those skilled in the art will recognize that such modifications will often be limited by the presence of interfering functionalities in the rest of the molecule and that it is preferred that such functionalizations be performed prior to coupling of the respective chemical "halves".

Intermediate compounds II, III, V, VI, VIII, IX, XI, XII, XIII, XIV, XVI, and XVII are either commercially available, known in the literature, or can be prepared according to methods known in the art.

Illustrative of the compounds of this invention are the following:

5-[4-(2-propyl-3,4-dichlorophenyl)butylthio]tetrazole,
N-methyl-8-(2-octyl-3-hydroxy-4-fluorophenyl)octanoic acid amide,
5-[2-(2-allyl-3-chloro-4-acetylphenylthio)ethylsulfonyl]tetrazole,
5-(2-propyl-3,4-dichlorophenoxy)pentanoic acid,
5-(2-methyl-3,4-difluorobenzyloxy)-1-pentanol,
S-[10-(2-hexyl-3-chloro-4-fluorophenylsulfinyl)decyl]isothiuronium bromide,
5-[6-(2-propyl-3-chloro-4-butanoylphenyl)-hex5-enylthion ]-tetrazole,
N,N-diethyl-6-(2-ethyl-3-hydroxy-4-iodophenoxy)undecanoic acid amide,
4-(2-propyl-3,4-dichlorobenzyloxy)butanoic acid,
N-(7-[2-isopropyl-3-iodo-4-(4-methoxybenzoyl)benzylthio]octyl)morpholine,
5-[2-(2-propyl-3,4-dichlorobenzyloxy)ethylthio]-tetrazole,
5-(2-allyl-3-fluoro-4-iodophenyl)-3-methyl-3-benzylpentanoic acid,
5-[4-(2-methyl-3-bromo-4-propionyl-methylbenzyloxy)butyl]-tetrazole,
5-[(2-propyl-3,4-dichlorobenzyloxy)propyl]tetrazole,
5-[6-(2-methyl-3,4-diiodobenzylsulfinyl)hexyloxy]-tetrazole,
6-(2-propyl-3,4-dichlorophenyl)hexanoic acid,
5-[3-(2-ethyl-3,4-dichlorophenyl)prop-2-enyl]tetrazole,
5-(3-(2-nonyl-3-hydroxy-4-fluorophenyl)hexylsulfonyl]tetrazole,
5-[4-(2-isopropyl-3,4-dichlorophenoxy)butylamino]-tetrazole,
5-[3-(2-butyl-3-iodo-4-fluorobenzylthio)propylthio]-tetrazole,
5-[3-(2-propyl-3,4-dichlorobenzylamino)propylthio]-tetrazole,
5-[4-(2-[3-hydroxypropyl]-3,4-dichlorobenzyloxy)-butyl]-tetrazole,
5-[N-methyl-3-(2-methyl-3,4-difluorophenyl)-propylamino]-tetrazole,
5-[4-(2-propyl-3,4-dichlorophenoxy)butyl]- tetrazole,
5-[3-(2-butenyl-3-hydroxy-4-chloro-α-ethylbenzyloxy)propylsulfonyl]-tetrazole,
5-[5-(2-propyl-3,4-dichlorophenyl)pentyl]- tetrazole,
10-(2-propyl-3,4-dichlorophenyl)undecanoic acid,
4-(2-butyl-3-iodo-4-bromophenyl)-3-phenylhexanoic acid,
8-(2-allyl-3-hydroxy-4-chlorophenyl)-7,8dimethyl-decanoic acid amide,
3-(2-propyl-3,4-dichloro-α-methylbenzylthio)propionic acid,
4-(2-allyl-3-chloro-4-cyclohexanoyl)pentanoic acid,
methyl 3-[2-(3-hydroxypropyl)-3-bromo-4-fluorophenylsulfonyl]octanoate
5-(4-[2-propyl-3-chloro-4-(4-chlorobenzoyl)benzyloxy]-butylamino)-tetrazole, and
4-(2-propyl-3,4-dichlorophenyl)-3-butenoic acid.

The following examples further illustrate the preparation of the starting materials, intermediates, and compounds of this invention. The examples are illustrative only and are not intended to limit the scope of the invention. Where structures were confirmed by proton nuclear magnetic resonance analysis, the compound is so designated by "NMR".

EXAMPLE 1

6-(2-Propyl-3,4-dichlorophenoxy)hexanoic acid

A. Preparation of 2-allyl-3,4-dichlorophenol

A solution of 100 g. of 3,4-dichlorophenol, 50 ml. of allyl bromide, 84 g. of potassium carbonate, and 1.0 g. of potassium iodide in 500 ml. of methyl ethyl ketone was allowed to reflux overnight. The solution was then cooled, filtered, and evaporated to dryness. The residue was then heated at 200° C. for approximately four hours. NMR analysis indicated that the 113.6 g. of remaining material was primarily the desired 2-allyl-3,4-dichlorophenol.

B. Preparation of 2-propyl-3,4-dichlorophenol

A solution of 117.5 g. of 2-allyl-3,4-dichlorophenol in 880 ml. of toluene was treated with about 8 g. of Raney nickel and hydrogenated at room temperature for three hours. The solution was filtered and evaporated. Purification of the residue using high pressure liquid chromatography (silica gel eluting with 4% ethyl acetate in hexane) provided the desired title compound together with small amounts of 2-propyl-4,5-dichlorophenol. NMR.

C. Preparation of 6-(2-propyl-3,4-dichlorophenoxy)hexanoic acid

To a solution of 1.1 g. of 2-propyl-3,4-dichlorophenol in 30 ml. of tetrahydrofuran and 30 ml. of hexamethylphosphoramide were added 4.1 g. of 6bromohexanoic acid. To the solution were then added 1.3 g. of a 50% oil dispersion of sodium hydride. A catalytic amount of potassium iodide was added and the reaction was stirred under a nitrogen atmosphere at 60°-70° C. overnight. The reaction was cooled to room temperature and ethyl acetate and water were added. The solution was evaporated to dryness. Fresh ethyl acetate and water were added and the layers were separated. Fresh ethyl acetate was added to the aqueous layer and the aqueous layer was adjusted to pH 2. The layers were separated and the organic layer was washed with a saturated sodium chloride solution. The organic layer was then filtered through sodium sulfate and evaporated to dryness. The resulting residue was extracted with hexane and evaporated to dryness to afford 500 mg. of the title compound.

EXAMPLE 2

5-[4-(2-Propyl-3,4-dichlorophenoxy)butyl]- tetrazole

A. Preparation of 4-(2-propyl-3,4-dichlorophenoxy)butane nitrile

To a solution of 37.1 g. of 2-propyl-3,4-dichlorophenol in 400 ml. of dry tetrahydrofuran and 25 ml. of hexamethylphosphoramide were added 32 ml. of 5- bromovaleronitrile. Sodium hydride (7.2 g. of a 60% dispersion in mineral oil) was added and the reaction was stirred for about three days at 65° C. The reaction mixture was cooled to room temperature and ethyl acetate and water were added. The solution was evaporated and ethyl acetate and water were added. The layers were separated and the ethyl acetate was washed several times with dilute hydrochlorid acid. The organic layer was filtered through sodium sulfate and evaporated to provide the desired nitrile intermediate. NMR.

B. Preparation of 5-[4-(2-propyl-3,4-dichlorophenoxy)butyl]-tetrazole

To a solution of 10.2 g. of 4-(2-propyl-3,4dichlorophenoxy)butane nitrile in 80 ml. of dimethylformamide were added 23.27 g. of sodium azide and 18.97 g. of ammonium chloride. The reaction was stirred for about two days at 120° C. under a nitrogen atmosphere. The reaction mixture was cooled to room temperature and ethyl acetate and water were added. The pH was adjusted to 2 and the layers were separated.

The ethyl acetate layer was washed several times with a saturated sodium chloride solution, filtered through sodium sulfate, and evaporated to dryness. Trituration of the residue with hexane followed by filtration provided 47.9 g. of the title product. NMR.

Analysis: $C_{14}H_{18}Cl_2N_4O$:
Calc.: C, 51.07; H, 5.51; N, 17.02; O, 4.86; Cl, 21.54
Found: C, 50.58; H, 5.54; N, 18.42; O, 5.56; Cl, 20.24.

EXAMPLE 3

5-[5-(2-Propyl-3,4-dichlorophenoxy)pentyl]- tetrazole

A. Preparation of 5-(2-propyl-3,4-dichlorophenoxy)pentyl bromide

To a solution of 3.12 g. of 2-propyl-3,4dichlorophenol in 30 ml. of dry tetrahydrofuran and 30 ml. of dry hexamethylphosphoramide were added 0.72 g. of a 50% sodium hydride dispersion in oil. Two milliliters of 1,5-dibromopentane were then added followed by a catalytic amount of potassium iodide. The reaction was stirred overnight under a nitrogen atmosphere at 60°-70° C. The reaction was then cooled to room temperature, ethyl acetate and water were added, and the solution was evaporated to dryness. Ethyl acetate and water were added to the residue and the layers were separated. The ethyl acetate layer was washed with dilute acid to remove residual hexamethylphosphoramide. The ethyl acetate was then washed with a saturated sodium chloride solution, filtered through sodium sulfate, and evaporated to dryness. The residue was purified by high pressure liquid chromatography to provide 1.6 g. of the desired bromo intermediate. NMR.

B. Preparation of 5-(2-propyl-3,4-dichlorophenoxy)pentane nitrile

A solution of 1.6 g. of 5-(2-propyl-3,4dichlorophenoxy)pentyl bromide and 0.22 g. of sodium cyanide were heated overnight at 75°-85° C. in 50 ml. of dimethylformamide. The solution was evaporated in vacuo and ethyl acetate and water were added to the residue. The layers were separated and the organic layer was washed several times with a saturated sodium chloride solution. The organic solution was filtered through sodium sulfate and evaporated to dryness to give 1.38 g. of the desired sub-title intermediate. NMR.

C. Preparation of 5-[5-(2-propyl-3,4-dichlorophenoxy) pentyl]-tetrazole

Following the procedure of Example 2B, 1.34 g. of 5-(2-propyl-3,4-dichlorophenoxy)pentane nitrile were transformed into the desired title product. NMR.

Analysis: $C_{15}H_{20}Cl_2N_4O$:
Calc.: C, 52.59; H, 5.87; N, 16.32. O, 4.66; Cl, 20.66.
Found: C, 52.83; H, 5.08; N, 16.03; O, 4.86; Cl, 20.43.

EXAMPLE 4

5-[6-(2-Propyl-3,4-dichlorophenoxy)hexyl]- tetrazole

Following the procedure of Example 3, 7.8 g. of 2-propyl-3,4-dichlorophenol and 5.9 ml. of 1,6-dibromohexane were transformed into 3.16 g. of the title product. NMR.

Analysis: $C_{16}H_{22}Cl_2N_4$:
Calc.: C, 53.72; H, 6.21; N, 15.68; O, 4.48; Cl, 19.85.
Found: C, 53.89; H, 6.18; N, 15.72; O, 4.69; Cl, 20.11.

EXAMPLE 5

5-[4-(2-Propyl-3-chloro-4-acetylphenoxy)butyl]-tetrazole

Following the procedure of Example 1A, 50 g. of 3-chlorophenol and 32 ml. of allyl bromide were heated with 42 g. of potassium carbonate and a catalytic in 250 ml. of methyl lytic amount of potassium iodide ethyl ketone. After evaporation the residue was heated to approximately 200° C. for 2-3 hours to give 62.8 g. of a mixture of 2- and 6-allyl-3-chlorophenol. Following Example 1B, this mixture was hydrogenated in the presence of 7 g. of Randy nickel in 530 ml. of toluene. Chromatography of the resulting products provided both the desired 2-propyl-3-chlorophenol and the by-product 2-propyl-5-chlorophenol.

Five and seven-tenths grams of 2-propyl3-chlorophenol were then reacted with 5.9 ml. of 5bromovaleronitrile following the procedure of Example 2A. The resulting 4-(2-propyl-3-chlorophenoxy)butane nitrile was provided by chromatography. This purified nitrile intermediate (3.3 g.) was dissolved in about 65 ml. of methylene chloride to which 3.0 g. of aluminum chloride and 1.7 ml. of acetyl chloride had been added and the reaction was heated to reflux overnight. The reaction was cooled, additional methylene chloride was added, and the mixture was poured into ice/hydrochloric acid. The layers were separated and the organic layer was washed first with an aqueous sodium bicarbonate solution and then with water. The organic solution was dried over sodium sulfate and evaporated to dryness. Purification by chromatography provided 2.67 g. of the desired 4-(2-propyl-3-chloro4-acetylphenoxy)butane nitrile. NMR.

A solution of 0.5 g. of 4-(2-propyl-3- chloro-4-acetylphenoxy)butane nitrile and 1.3 g. of tetramethylguanidinium azide in 3 ml. of dimethylformamide was heated overnight at 125° C. The reaction was cooled, ethyl acetate and water were added, and the layers were separated. Water was added to the ethyl acetate layer, the water layer was acidified, and the layers were separated. The ethyl acetate was dried and evaporated to dryness. The residue was purified by chromatography to give the desired title product. NMR.

Analysis: $C_{16}H_{21}ClN_4O_2$.
Calc.: C, 57.06; H, 6.28; N, 16.63.
Found C, 58.58; H, 6.57; N, 14.71.

EXAMPLE 6

5-[6-(2-Octyl-3,4-dichlorophenoxy)hexyl]- tetrazole

A. Preparation of 2,3-dihydro-2-hydroxy-4,5-dichlorobenzofuran.

A solution of 20.3 g. of 2-allyl-3,4-dichlorophenol in methylene chloride was ozonized for 30 minutes at −78° C. The solution was warmed to −23° C. and ozonized an additional ten minutes. Dimethyl sulfide was added to the reaction and the solution was then evaporated to dryness. Purification by high pressure liquid chromatography afforded 1.3 g. of 2,3-dihydro-2-hydroxy-4,5-dichlorobenzofuran as white crystals.

B. Preparation of 2-(2-octenyl)-3,4-di- chlorophenol

Twenty-five grams of n-hexyltriphenylphosphonium bromide were dissolved in 350 ml. of dry tetrahydrofuran and cooled to −10° C. To the solution were added 37 ml. of a 1.6M solution of n-butyllithium in hexane. The solution was slowly warmed to room temperature and stirred for one hour. The solution was then cooled to 0° C. and a solution of 2.38 g. of 2,3- dihydro-2-hydroxy-4,5-dichlorobenzofuran in 20 ml. of tetrahydrofuran was added. The reaction was allowed to reflux for approximately 18 hours. The solution was then cooled and evaporated to dryness. Ethyl acetate and water were added and the pH was adjusted to 2.5. The layers were separated. The organic layer was washed with a saturated sodium chloride solution, filtered through sodium sulfate, and evaporated to dryness. The residue was purified by high pressure liquid chromatography giving 2.51 g. of the desired intermediate as a mixture of cis and trans isomers.

C. Preparation of 2-octyl-3,4-dichlorophenyl.

A solution of 1.08 g. of 2-(2-octenyl)-3,4-dichlorophenol in 50 ml. of toluene was hydrogenated in the presence of Raney nickel. The catalyst was removed by filtration and the solvent was evaporated to dryness affording 1.04 g. of 2-octyl-3,4-dichlorophenol. NMR.

D. Preparation of 5-[6-(2-octyl-3,4-dichlorophenoxy)hexyl]-tetrazole

Following the procedures of Example 3, 775 mg. of 2-octyl-3,4-dichlorophenol and 0.43 ml. of 1,6-dibromohexane were transformed into 10.6 mg. of the title product. The NMR spectrum was consistent with the structure of the desired product.

EXAMPLE 7

5-[5-(2-Dodecyl-3,4-dichlorophenoxy)pentyl]tetrazole

Following the general procedures of Example 6, 2,3-dihydro-2-hydroxy-4,5-dichlorobenzofuran and n-decyltriphenylphosphonium bromide were transformed into the title product. The NMR spectrum was consistent with the structure of the desired product.

EXAMPLE 8

5-[3-(2-Propyl1-3,4-dichlorophenoxy)propanethio]-tetrazole

Following the procedure of Example 3A, 3-(2- propyl-3,4-dichlorophenoxy) propyl bromide was prepared from 2-propyl-3,4-dichlorophenol and 1,3-dibromopropane. A solution of 1.96 g. of 3-(2-propyl-3,4-dichlorophenoxy)propyl bromide, 1.66 g. of potassium carbonate, and 0.615 g. of 5-mercaptotetrazole in 20 ml. of dimethylformamide was stirred overnight at room temperature. Ethyl acetate and water were added and the layers were separated. The organic layer was washed successively with dilute acid, dilute potassium carbonate solution, and again with dilute acid. The organic solution was dried over sodium sulfate and evaporated to dryness. The residue was washed several times with water to provide 295 mg. of the desired title product. NMR.

Analyis: $C_{13}H_{16}Cl_2N_4OS$.

Calc.: C, 44.96; H, 4.64; N, 16.13; S, 9.23.

Found: C, 45.12; H, 4.57; N, 16.14; S, 9.41.

EXAMPLE 9

6-(2-Pentyl-3,4-dichlorophenoxy)hexanoic acid

Following the general procedure of Example 6B, 2.3 g. of 2,3-dihydro-2-hydroxy-4,5-dichlorobenzofuran and 17.3 g. of propyltriphenylphosphonium bromide were reacted to provide 840 mg. of 2-(2-pentenyl)-3,4-dichlorophenol which upon hydrogenation following the procedure of Example 6C provided 300 mg. of 2-pentyl-3,4-dichlorophenol. This phenol was then reacted with 5.1 mmoles of 6-bromohexanoic acid following the procedure of Example 1C to provide 58 mg. of the desired title product. NMR.

EXAMPLE 10

6-[2-(2-Hydroxyethyl)-3,4-dichlorophenoxy]hexanoic acid

A. Preparation of 2-(2-hydroxyethyl)-3,4-dichlorophenol

A solution of 2.26 g. of 2,3-dihydro-2-hydroxy-4,5-dichlorobenzofuran in 15 ml. of absolute ethanol was cooled to 0° C. by means of an external ice bath. Three millimoles (114 mg.) of sodium borohydride were added to the solution and the reaction was stirred while allowing the reaction to warm to room temperature. The mixture was evaporated under reduced pressure and water and ethyl acetate were added to the residue. The pH of the aqueous layer was adjusted to 2.5 with the addition of acid and the layers were separated. The ethyl acetate layer was dried and evaporated to provide the subtitle intermediate phenol which was used without further purification.

B. Preparation of 6-[2-(2-hydroxyethyl)-3,4dichlorophenoxy]hexanoic acid

Following the procedure of Example 1C, two millimoles each of 2-(2-hydroxyethyl)-3,4-dichlorophenol and 6-bromohexanoic acid were reacted to provide 55 mg. of the desired title product which crystallized from methylene chloride.

EXAMPLE 11

5-[4-(2-Propyl-3-hydroxy-4-chlorophenoxy)butyl]-tetrazole

A. Preparation of 5-[4-(2-propyl-3-hydroxyphenoxy)butyl]-tetrazole

Six grams of 2-propylresorcinol and 6.4 g. of 5-bromovaleronitrile were reacted following cedure of Example 2A to provide 3.4 g. of the desired nitrile intermediate. This intermediate was heated to 125° C. overnight with 40 mmoles of tetramethylguanidinium azide in 10 ml. of dimethylformamide. The solvent was removed under reduced pressure and the residue was dissolved in ethyl acetate. The organic solution was washed with water adjusted to pH 6. The organic layer was dried and evaporated to yield the desired subtitle tetrazole intermediate which crystallized after evaporation of the solvent. NMR.

B. Preparation of 5-[4-(2-propyl-3-hydroxy-4-chlorophenoxy)butyl]-tetrazole

A solution of 1.38 g. of 5-[4-(2-propyl-3-hydroxyphenoxy)butyl]-tetrazole in 25 ml. of tetrahydrofuran was cooled to −10° C. by means of an external alcohol-ice bath. One millimole of sulfuryl chloride was slowly added and the reaction mixture was stirred for one hour. The mixture was evaporated under reduced pressure and the residue was triturated with diethyl ether. The ether was evaporated and the residue was purified by reverse phase high pressure liquid chromatography. The appropriate fractions provided 42 mg. of the desired title product plus 92 mg. of the 2-propyl-3-hydroxy-6-chlorophenoxy isomer and a small amount of the 2-propyl-3-hydroxy-4,6-dichlorophenoxy compound.

EXAMPLE 12

7-(2-Propyl-3,4-dichlorophenoxy)heptanoic acid

A solution of 3.09 g. of 2-propyl-3,4-dichlorophenol, 3.1 g. of 7-bromoheptanoic acid, 3.1 g. of potassium carbonate, and 2.0 g. of potassium iodide in 50 ml. of methyl ethyl ketone was heated at reflux overnight. The reaction mixture was cooled to room temperature and evaporated in vacuo. Ethyl acetate and water were added to the residue and the layers were separated. Fresh water was added to the organic layer, the pH was adjusted to 2.0 with acid, and the layers were separated. The organic layer was washed with a saturated sodium chloride solution, filtered through sodium sulfate, and evaporated to dryness to give 4.68 g. of the desired title product.

Analysis: $C_{16}H_{22}Cl_2O_3$.

Calc.: C, 57.67; H, 6.65; O, 14.40; Cl, 21.28.

Found: C, 55.85; H, 6.59; O, 15.81; Cl, 20.33.

The compounds of Formula I should be useful in treating any condition, including clinical conditions, which is characterized by excessive release of leukotrienes $C_4$, $D_4$, or $E_4$. These conditions include immediate type hypersensitivity reactions such as asthma. Evidence obtained over the past few years has shown the presence of leukotrienes in sputum of patients with chronic bronchitis (Turnbull, et al., *Lancet* II, 526 (1977)) and cystic fibrosis (Cromwell, et al., Lancet II, 164 (1981)), suggesting a role of leukotrienes in the pathology of those diseases. Furthermore, Lewis and colleagues [*Int. J. Immunopharmacology* 4, 85 (1982)] have recently detected material in rheumatoid synovial fluid that reacts antigenically with antibody to $LTD_4$. This may hallmark the existence of leukotriene permeability factors that, together with $LTB_4$, augment the inflammatory process in the diseased joints. Therefore, the compounds described in this invention should also alleviate some of the symptoms of chronic bronchitis and cystic fibrosis and possibly rheumatoid arthritis by virtue of their ability to antagonize leukotrienes.

The term "excessive release" of leukotrienes refers to an amount of leukotrienes sufficient to cause the particular condition associated with such amount. The amount of leukotriene which is considered to be excessive will depend on a variety of factors, including the specific leukotriene(s) involved, the amount of leukotriene required to cause the particular condition, and the species of the mammal involved. As will be appreciated by those skilled in the art, the success of treating a mammal suffering from or susceptible to a condition characterized by an excessive release of leukotrienes with a compound of Formula I will be measured by the regression or prevention of the symptoms of the condition.

Leukotriene antagonism was demonstrated by the following test procedure:

Male, Hartley guinea pigs weighing 200–450 grams were killed by decapitation. A section of terminal ileum was removed, the lumen cleaned, and the tissue divided into 2.5 cm. segments. The ilea were mounted in 10 ml. tissue baths containing Krebs-bicarbonate solution of the following composition in mmoles/ liter: KCl, 4.6; $CaCl_2 \cdot 2H_2O$, 1.2; $KH_2PO_4$, 1.2; $MgSO_4 \cdot 7H_2O$, 1.2; NaCl, 118.2; $NaHCO_3$, 24.8; and dextrose, 10.0. The bath fluid was maintained at 37° C. and aerated with 95 percent oxygen and 5 percent $CO_2$. In addition, the buffer contained $1 \times 10^{-6}M$ atropine to reduce ileal spontaneous activity. Isometric measurements were made with a Grass FTO3C force-displacement transducer and recorded on a Grass polygraph as change in grams of force. A passive force of 0.5 g. was applied to the tissues. After an appropriate equilibration period, single submaximal control responses to pure $LTD_4$ were obtained. Following a five minute exposure of the ileum to an experimental drug, the control concentration of $LTD_4$ was added to the tissue bath. The response of the ileum to $LTD_4$ in the presence of the drug was compared to the response in the absence of the drug. For some of the drugs in this series a more detailed analysis of $LTD_4$ antagonism was made. In these experiments, cumulative concentration-response curves were obtained to $LTD_4$ in guinea pig ileum and trachea. This was followed by a 30 minute incubation with various concentrations of the experimental drug. The concentration response curve to $LTD_4$ was then repeated in the presence of the antagonist. Only one concentration of antagonist was used on a single tissue. $K_B$ values were calculated by the method of Furchgott [*Ann. N.Y. Acad. Sci.*, 139, 553 (1967)] using the following equation.

$$K_B = \frac{[\text{Antagonist}]}{\text{Dose Ratio} - 1}$$

Dose ratio refers to the concentration of agonist required to elicit 50 percent of the maximal response ($ED_{50}$) in the presence of the antagonist divided by the $ED_{50}$ in the absence of the antagonist. Calculations were performed with the aid of a computer and a digital plotter. The $pA_2$ is then calculated as the negative log of $K_B$ when the slope of the Schild plot is not significantly different from unity.

The testing of the compounds of Formula I in these two test procedures is summarized in Table I.

TABLE I

| Compound of Example No. | Percent inhibition of $LTD_4$ evoked ileal contractions | | | | pA2 |
|---|---|---|---|---|---|
| | Compound concentration | | | | |
| | $3 \times 10^{-6}$ M | $1 \times 10^{-6}$ M | $3 \times 10^{-7}$ M | $1 \times 10^{-7}$ M | |
| 1 | 78 | 51 | | | |
| 2 | | 94 | 70 | 56 | 7.0 |
| 3 | 92 | 75 | 51 | | 6.6* |

TABLE I-continued

| Compound of Example No. | Percent inhibition of LTD$_4$ evoked ileal contractions | | | | |
|---|---|---|---|---|---|
| | Compound concentration | | | | |
| | $3 \times 10^{-6}$ M | $1 \times 10^{-6}$ M | $3 \times 10^{-7}$ M | $1 \times 10^{-7}$ M | pA2 |
| 4 | 96 | 84 | | | 7.0* |
| 5 | | | 73 | 49 | 6.98* |
| 6 | 59 | 53 | | | |
| 7 | 16 | | | | |
| 8 | | | 79 | 59 | |
| 9 | 57 | 21 | | | |
| 10 | 22 | | | | |
| 11 | 20 | | | | 5.5* |
| 12 | 31 | | | | |

*estimated.

The compounds or formulations of the present invention may be administered by the oral and rectal routes, topically, parenterally, e.g., by injection and by continuous or discontinuous intra-arterial infusion, in the form of, for example, tablets, lozenges, sublingual tablets, sachets, cachets, elixirs, suspensions, aerosols, ointments, for example, containing from 1 to 10% by weight of the active compound in a suitable base, soft and hard gelatin capsules, suppositories, injectable solutions and suspensions in physiologically acceptable media, and sterile packaged powders adsorbed onto a support material for making injectable solutions. Advantageously for this purpose, compositions may be provided in dosage unit form, preferably each dosage unit containing from about 5 to 500 mg. (from about 5 to 50 mg. in the case of parenteral or inhalation administration, and from about 25 to 500 mg. in the case of oral or rectal administration) of a compound of Formula I. Dosages of from about 0.5 to 300 mg./kg. per day, preferably 0.5 to 20 mg./kg., of active ingredient may be administered although it will, of course, readily be understood that the amount of the compound or compounds of Formula I actually to be administered will be determined by a physician, in the light of all the relevant circumstances including the condition to be treated, the choice of compound to be administered and the choice of route of administration and therefore the above preferred dosage range is not intended to limit the scope of the present invention in any way.

The formulations of the present invention normally will consist of at least one compound of Formula I mixed with a carrier, or diluted by a carrier, or enclosed or encapsulated by an ingestible carrier in the form of a capsule, sachet, cachet, paper or other container or by a disposable container such as an ampoule. A carrier or diluent may be a solid, semisolid or liquid material which serves as a vehicle, excipient or medium for the active therapeutic sub- stance.

Some examples of the diluents or carrier which may be employed in the pharmaceutical compositions of the present invention are lactose, dextrose, sucrose, sorbitol, mannitol, propylene glycol, liquid paraffin, white soft paraffin, kaolin, fumed silicon dioxide, microcrystalline cellulose, calcium silicate, silica, polyvinylpyrrolidone, cetostearyl alcohol, starch, modified starches, gum acacia, calcium phosphate, cocoa butter, ethoxylated esters, oil of theobroma, arachis oil, alginates, tragacanth, gelatin, syrup, methyl cellulose, polyoxyethylene sorbitan monolaurate, ethyl lactate, methyl and propyl hydroxybenzdate, sorbitan trioleate, sorbitan sesquioleate and oleyl alcohol and propellants such as trichloromonofluoromethane, dichlorodifluoromethane and dichlorotetrafluoroethane. In the case of tablets, a lubricant may be incorporated to prevent sticking and binding of the powdered ingredients in the dies and on the punch of the tableting machine. For such purpose there may be employed for instance aluminum, magnesium or calcium stearates, talc or mineral oil.

Preferred pharmaceutical forms of the present invention are capsules, tablets, suppositories, injectable solutions, creams and ointments. Especially preferred are formulations for inhalation application, such as an aerosol, and for oral ingestion.

I claim:

1. A compound of the formula

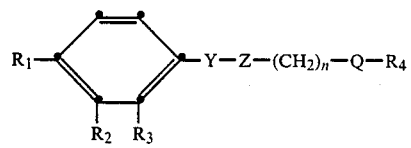

and pharmaceutically acceptable salts thereof, wherein:
$R_1$ is

or halo;
$R_2$ is halo or hydroxy;
$R_3$ is $C_1$-$C_{12}$ alkyl, hydroxy-substituted $C_1$-$C_{12}$ alkyl, or $C_2$-$C_6$ alkenyl;
Y is —O—
Z is —$CR_8R_9$—
Q is —O—, —NR—,

or a bond; $R_4$ is —$COR_{10}$ or

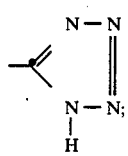

where
R is hydrogen or $C_1$-$C_3$ alkyl;
$R_5$ is $C_1$-$C_6$ alkyl, $C_3$-$C_8$ cycloalkyl, or phenyl optionally substituted with a group selected from halo, $C_1$-$C_4$ alkyl, or $C_1$-$C_4$ alkoxy; is independently hydrogen, $C_1$-$C_{10}$ alkyl, phenyl, or benzyl;
$R_{10}$ is hydroxy; and
p is 0, 1, or 2;
with the provisions that:
(a) when $R_1$ is

$R_2$ may not be hydroxy; and
(b) when $R_4$ is —$COR_{10}$, Q may only be a bond.

2. A compound of claim 1 wherein $R_1$ and $R_2$ are both chloro.

3. A compound of claim 2 of the formula

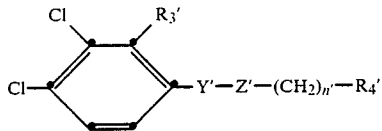

and pharmaceutically acceptable salts thereof wherein:
$R_3'$ is $C_1$-$C_6$ alkyl;
Y' is —O— and Z' is —CH$_2$—;
0 n' is 2 or 3; and
$R_4'$ is —COOH, 5-tetrazolyl, or 5-thiotetra-zolyl.

4. A compound of claim 3 wherein $R_3'$ is propyl.

5. The compound of claim 4 which is 5-(2-propyl-3,4-dichlorophenoxy) pentanoic acid or a pharmaceutically acceptable salt thereof.

6. The compound of claim 4 which is 4-(2-propyl-3,4-dichlorobenzyloxy) butanoic acid or a pharmaceutically acceptable salt thereof.

7. The compound of claim 4 which is 6-(2-propyl-3,4-dichlorophenyl) hexanoic acid or a pharmaceutically acceptable salt thereof.

8. The compound of claim 4 which is 5-[4(2-propyl-3,4-dichlorophenoxy)butyl]-tetrazole or a pharmaceutically acceptable salt thereof.

9. The compound of claim 4 which is 5-[3(2-propyl-3,4-dichlorobenzyloxy)propyl]-tetrazole or a pharmaceutically acceptable salt thereof.

10. The compound of claim 4 which is 5-[5(2-propyl-3,4-dichlorophenyl)pentyl]-tetrazole or a pharmaceutically acceptable salt thereof.

11. The compound of claim 4 which is 5-[3-(2-propyl-3,4-dichlorophenoxy)propylthio]-tetrazole or a pharmaceutically acceptable salt thereof.

12. The compound of claim 4 which is 5-[2-(2-propyl-3,4-dichlorobenzyloxy)ethylthio]-tetrazole or a pharmaceutically acceptable salt thereof.

13. The compound of claim 4 which is 5-[4-(2-propyl-3,4-dichlorophenyl)butylthio]-tetrazole or a pharmaceutically acceptable salt thereof.

14. A method of treating a mammal suffering from or susceptible to any condition characterized by an excessive release of leukotrienes, which comprises administering to said mammal a leukotriene antagonizing amount of a compound of claim 1.

15. A method of treating a mammal suffering from or susceptible to any condition characterized by an excessive release of leukotrienes, which comprises administering to said mammal a leukotriene antagonizing amount of a compound of claim 4.

16. A method of treating a mammal suffering from or susceptible to an immediate hypersensitivity reaction of the type represented by asthma, which comprises administering to said mammal a therapeutically-effective amount of a compound of claim 1.

17. A pharmaceutical formulation comprising a compound of claim 1 in association with a pharmaceutically acceptable carrier.

18. A pharmaceutical formulation comprising a compound of claim 4 in association with a pharmaceutically acceptable carrier.

* * * * *